US011534624B2

(12) United States Patent
Kuefer et al.

(10) Patent No.: US 11,534,624 B2
(45) Date of Patent: Dec. 27, 2022

(54) CUSTOMIZATION OF A DOSE DISTRIBUTION SETTING FOR A TECHNICAL APPLIANCE FOR TUMOR THERAPY

(71) Applicant: FRAUNHOFER-GESELLSCHAFT ZUR FOERDERUNG DER ANGEWANDTEN FORSCHUNG E.V., Munich (DE)

(72) Inventors: Karl-Heinz Kuefer, Weilerbach (DE); Alexander Scherrer, Kaiserslautern (DE); Michael Monz, Mainz (DE); Philipp Suess, Kaiserslautern (DE); Michael Bortz, Kaiserslautern (DE)

(73) Assignee: FRAUNHOFER-GESELLSCHAFT ZUR FOERDERUNG DER ANGEWANDTEN FORSCHUNG E.V.

( * ) Notice: Subject to any disclaimer, the term of this patent is extended or adjusted under 35 U.S.C. 154(b) by 251 days.

(21) Appl. No.: 16/778,436

(22) Filed: Jan. 31, 2020

(65) Prior Publication Data
US 2020/0164226 A1 May 28, 2020

Related U.S. Application Data

(63) Continuation of application No. 13/989,448, filed as application No. PCT/IB2011/055249 on Nov. 23, 2011, now abandoned.

(30) Foreign Application Priority Data

Nov. 26, 2010 (DE) .......................... 102010060847.5
Nov. 27, 2010 (DE) .......................... 102010062079.3

(51) Int. Cl.
*A61N 5/10* (2006.01)

(52) U.S. Cl.
CPC .......... *A61N 5/1031* (2013.01); *A61N 5/103* (2013.01); *A61N 5/1045* (2013.01)

(58) Field of Classification Search
CPC .... A61N 5/103; A61N 5/1031; A61N 5/1037; A61N 5/1038; A61N 5/1039; A61N 5/1045; A61N 5/1047
See application file for complete search history.

(56) References Cited

U.S. PATENT DOCUMENTS 6,038,283 A 3/2000 Carol et al.
6,111,575 A 8/2000 Martinez et al.
(Continued)

FOREIGN PATENT DOCUMENTS

DE 102005058871 B3 7/2007
EP 2260902 A1 12/2010

OTHER PUBLICATIONS

M. Ehrgott, "An Optimisation Model for Intensity Modulated Radiation Therapy", Proc. of the 37th Annual ORDNZ Conference, 2002, pp. 23-31.
(Continued)

*Primary Examiner* — Carrie R Dorna
(74) *Attorney, Agent, or Firm* — Troutman Pepper Hamilton Sanders LLP; John A. Morrissett; Aaron E. Johnston

(57) ABSTRACT

The aim of the invention is to provide a planner with the opportunity to effect local improvement of an IMRT treatment plan which is available to him. To this end, a method for customizing a dose distribution setting for a technical appliance in tumor therapy is proposed.

22 Claims, 12 Drawing Sheets

(56) References Cited

U.S. PATENT DOCUMENTS

| | | |
|---|---|---|
| 6,219,403 B1 | 4/2001 | Nishihara |
| 7,391,026 B2 | 6/2008 | Trinkaus et al. |
| 7,593,505 B2 | 9/2009 | Saracen et al. |
| 2003/0212325 A1 | 11/2003 | Cotrutz et al. |
| 2005/0111621 A1 | 5/2005 | Riker et al. |
| 2006/0274885 A1 | 12/2006 | Wang et al. |
| 2007/0167748 A1 | 7/2007 | Rietzel |
| 2010/0054411 A1 | 3/2010 | Nord et al. |

OTHER PUBLICATIONS

C. Thieke et al., "A new concept for interactive radiotherapy planning with multicriteria optimization: First clinical evaluation", Radiotherapy and Oncology; vol. 85, No. 2; Nov. 1, 2007 (Nov. 1, 2007); pp. 292-298; XP022363696, ISSN: 0167-8140, DOI: 10.1016/J.RADONC.2007.06.020, Section "Second stage—exploring the Partero front", Section "Discussion".

Erwin Petter, International Search Report of International Application No. PCT/IB2011/055249; dated May 21, 2012.

Bernhard Steinbauer; German Examination Report; DE 10 2010 062 079.3; dated Jun. 9, 2012.

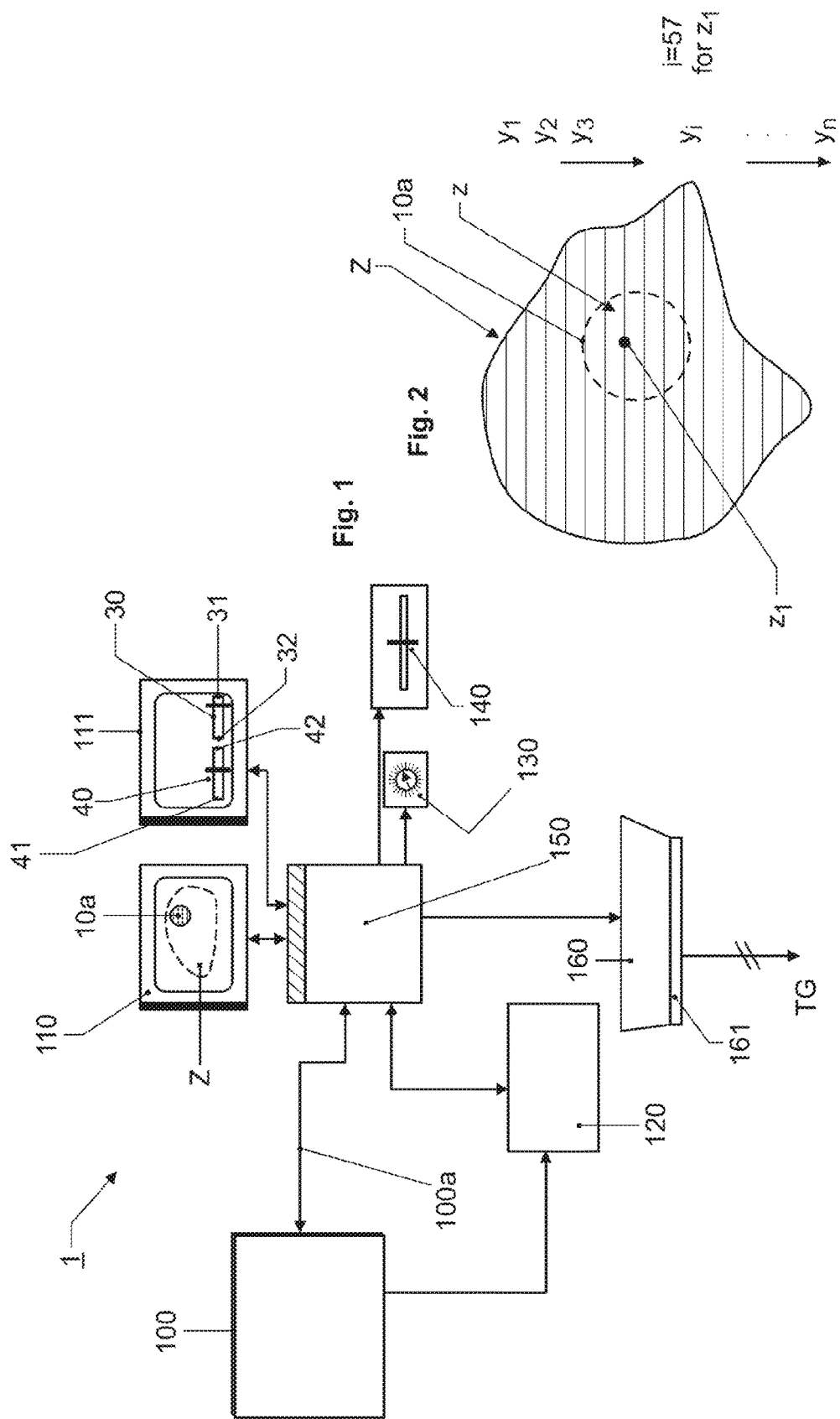

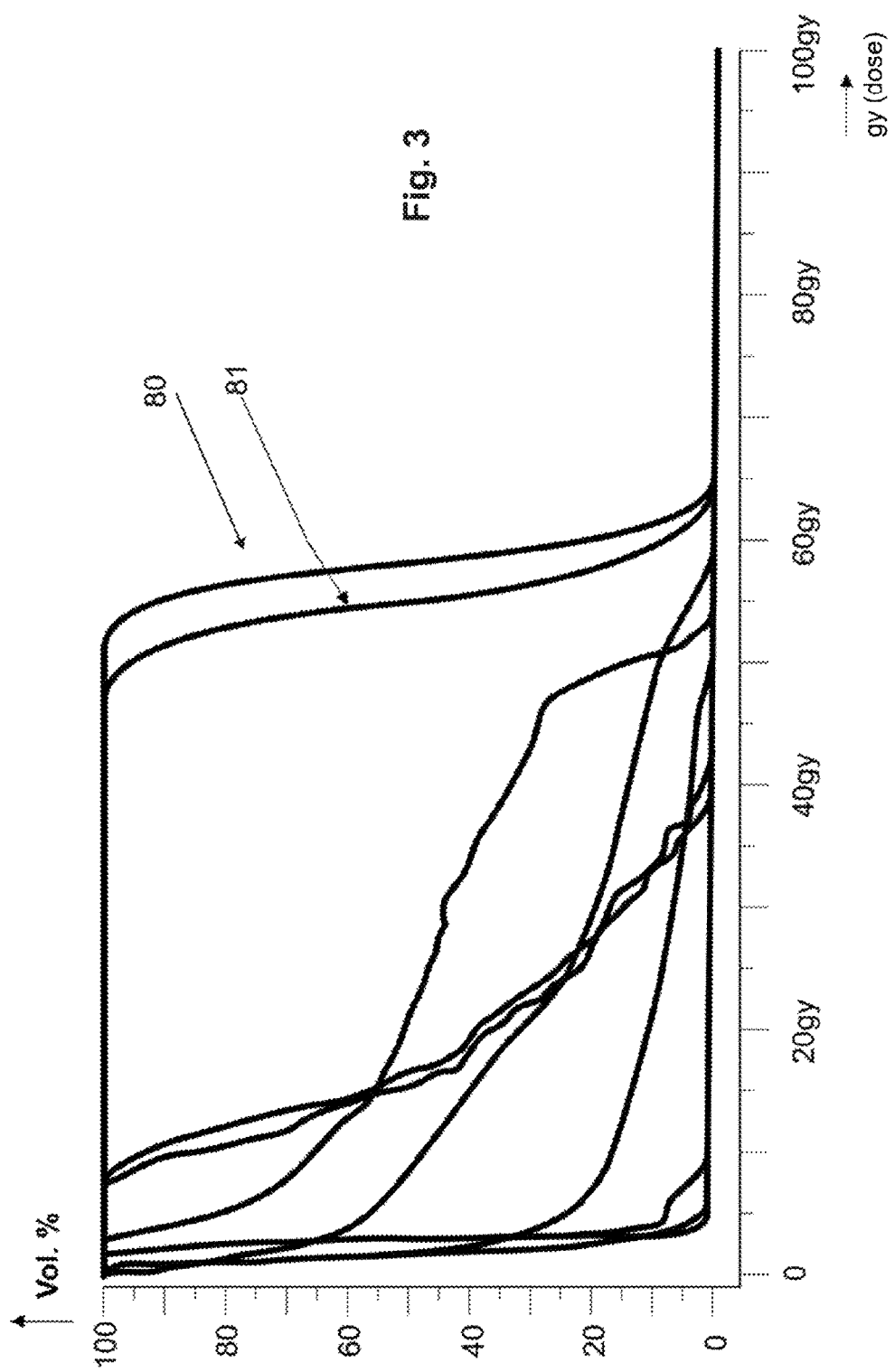

CUSTOMIZATION OF A DOSE DISTRIBUTION SETTING FOR A TECHNICAL APPLIANCE FOR TUMOR THERAPY

CROSS REFERENCE TO RELATED APPLICATION

This application is a continuation of, and claims priority under 35 U.S.C. § 120 to, U.S. patent application Ser. No. 13/989,448, filed Jul. 31, 2013, which is a National Stage Entry under 35 U.S.C. § 371 of International Patent Application No. PCT/IB11/55249, filed on Nov. 23, 2011, which claims priority to German Patent Application No. 10 2010 062 079.3, filed Nov. 27, 2010 and German Patent Application No. 10 2010 060 847.5, filed on Nov. 26, 2010. The entire contents of each are fully incorporated herein by reference.

FIELD OF THE INVENTION

The invention relates to a method for optimizing a set state of a device for tumor treatment. In particular, this involves a substantial improvement of an already patented system, cf. U.S. Pat. No. 7,391,026 B2. The plan finding control disclosed therein for determining an optimum plan for the treatment of a patient suffering from a tumor disease was a quantum jump. It was a reversal of the approaches suggested so far and has become generally known as IMRT in the field. The approach called "inverse therapy planning" has been suggested by Bortfeld, cf. U.S. Pat. No. '026 (as above), col. 1, line 43 et seq. In the course of application and practical testing thereof, possibilities of improvement have opened up over time which are the subject matter of this invention.

BACKGROUND OF THE INVENTION

When starting from the cited prior art, the planner finds a suitable plan by means of a design tool. The suitable plan is extensive and comprises setting parameters for the setting of (or: on) the therapeutic device which performs the tumor therapy on the patient at a later stage. It is correspondingly clear that the setting of this device and the generation or determination of the setting of the device is not yet a therapeutic treatment or a medical treatment as such, but a preliminary stage implemented long before. Setting parameters of technical nature are determined on the basis of which a therapy can be performed at a later stage and in a completely different location. The said IMRT calls these parameters a plan. The plan is simultaneously "a solution" selected from a variety of pre-calculated plans or solutions which are all suitable; however, only one of these is the optimum one for the planner. Selecting this optimum one from a variety of already available plans is enabled by virtue of the design tool according to U.S. Pat. No. 7,391,026.

Nevertheless, there is still need for improvement on the part of the planner. This need for improvement may relate to critical spots in the plan which can be changed in the plan itself only to the effect that another plan is selected. This other plan is changed with a view to an improvement in an "area of interest", however, is again one of the pre-calculated plans. Also this plan had already been calculated and provided in the database.

The invention starts from the object to enable a planner to locally improve an IMRT treatment plan available to him. A local improvement includes a plurality of definitions, for example, a local overdosing in a risk area or a local under-dosing in a target area. In a specific embodiment, the target area may refer specifically to the tumor to be provided with a dose as high as possible, and in another specific embodiment, the risk area may refer to a specific risk organ (in terms of space). However, also areas in tissue may be affected which are not defined in terms of an organ, but are defined in terms of area only. If one wishes to improve local deficiencies, one may also start, within the scope of the defining language, from the removal of "critical spots" or critical spot remover as an object enabled by the invention described and defined in the following. More abstract, the object is to remove critical spots (in both directions, towards under-dosing or overdosing) and to change the already present plan (the already selected solution) as little as possible. Precisely, none of the pre-calculated other solutions is to be used, but the initial solution is to be changed in a locally defined manner.

The object is as a method or arrangement for adjusting a dose distribution setting.

By the solution, the initial plan is locally changed, but not the entire plan. In this connection, a person skilled in the art would say that a local point, which may be referred to as small, is changed while practically maintaining the initial plan. If he used a new plan, he would change the localized critical areas (the critical spots), but also dislocate them and, as a rule, not really remove them. Thus, a too global change of the plan is avoided. In other words, the change in the "first plan" is to be kept as little as possible outside of the "critical spot".

This definition of the solution is oriented towards the term 'local change' or 'spot change', respectively, which spot is small in relation to the total volume.

Since the dose distribution plan involves computations with voxels, a local/small volume can include less than 500 voxels. This regional volume may be called spot or box. A voxel typically has an edge length of 3 mm. A preferred dimension of this local spot (box or spot) is less than 7×7×7 voxels in the three directions in space, i.e. less than approximately 350 voxels, or below an upper limit of 500 voxels. In other words, less than 5% of the volume affected by dose distribution as a plan volume is involved. The local/small volume (group of voxels) may comprises less than 500 voxels. The plan volume may comprise more than 2000 voxels.

The setting which makes adjustments on the technical device or adjusts the technical device for tumor therapy to such a therapy can be set with a plurality of technical parameters of various nature. In the IMRT method, multi-leaf heads using a plurality of strip-shaped setting sliders may provide a first setting, cf. FIG. 3 and associated description of U.S. Pat. No. '026, as mentioned at the beginning. Furthermore, radiation doses, angles of rotation for a rotating head, dwell times of the rotating head in specific locations and, of course, also combinations of the multi-leaf head setting with the mentioned other parameters may be specified. In a rough overview, the period of time (radiation time), the profile of a respective irradiation by the multi-leaf head and various positions of angles of incidence can be specified which fall under the term 'setting of the technical device for tumor therapy'. Photons, electrons, heavy ions or protons can be used as radiation, depending on the therapist, patient and available technical equipment as well as the kind and nature of the tumor area to be treated (to be irradiated), cf. again U.S. Pat. No. '026, paragraph [068] therein.

A plan, detailed explanations of which were provided in advance, is available for this treatment. This first plan is read out from a data memory, for example an ordered database, and illustrated on a monitor. There is a variety of possibilities of illustration depending on the nature of the user or his preferred selection criteria. In the examples described in the following, a DVH diagram and three sectional representations (transverse, sagittal and frontal) are explained which give a good overview on the radiation doses in the spatial distribution and convey some kind of mean value to the user enabling an overall assessment of a respective plan, the DVH diagram in the example. In general, the entire plan volume affected by the dose distribution is illustrated, wherein both, the target volume (the tumor area, one or a plurality thereof) and a number of risks or risk organs, which may also be present in form of areas independent of a physically defined risk organ, are located within this plan volume. In order to achieve the set object, a point having a dose value of an undesired level or an undesired weakness is specified in the illustrated plan. This "initial voxel" is a voxel located in the spatial area of, for example, the three sectional representations located perpendicularly to each other. It may be selected in the sagittal representation, in the transverse representation or in the frontal representation, however, relates to a spatial area defined as a box around this initial voxel. This serves the purpose of changing the illustrated plan in at least one area of fineness specified in terms of volume which is small as compared to the size of the plan volume. At this specified point and by means of the small/local group of voxels defined by the initial voxel, a change is to take place either in the upward direction towards higher radiation doses or in the downward direction towards lower radiation doses in the specified small area.

A causal follow-up plan as close to the illustrated plan as possible is supposed to result therefrom, i.e. which changes the DVH diagram to a small extent only, but which is to change the specified small point as an area of fineness specified in terms of volume.

According to the invention, this takes place precisely by not retrieving a new plan having a dose corresponding to a desired value in this area of fineness specified in terms of volume from the previously stored plans/solutions, since this plan will, with almost absolute certainty, involve very great differences in many other points which would cause a markedly different DVH which is precisely what is to be avoided according to the invention. By the selection of the specific point by means of the initial voxel, which can be identified by a cursor and is located in a layer of the plan volume, the group of voxels surrounding this initial voxel is determined.

According to the invention, the group is very small and its size can be defined as desired by the user. The selection of the initial voxel in a layer, as discussed above, relates to the sagital layers, the transverse layers or the frontal layers. However, after determination of the initial voxel, the group of voxels will extend into three-dimensional space, i.e. into all layers; however, it needs to be identified in one layer only.

In this connection, the user has the choice to determine the position of the initial voxel in one of the illustrated layers.

After determination of the initial voxel and the local group of voxels as the specified area of fineness in the considerably larger plan volume, a conversion is initiated. The conversion starts from the first plan illustrated. It is converted into a first navigation plan, wherein the first plan is the starting point (initial plan) and the change in dose in the specified area of fineness is taken into account. Such a conversion of a plan can be performed, for example, in the same way as the pre-calculated plans in the database are calculated for a variety of possible solutions. The associated method is publicly accessible and may be found in Philipp Suess, A primal-dual barrier algorithm for the IMRT planning problem—An application for optimization-driven adaptive discretization, Mensch and Buch Verlag (mbv), Berlin, 2008.

The thus generated first navigation plan is not a "new" plan in the sense of the plans/solutions of the pre-calculated potential in the data memory, but a converted first plan. Only the first plan comes out as a plan from the data memory acting as a database and is illustrated to select the initial voxel therefrom, at the position or around the position of which a local change in dose is to be effected. Thus, when the first plan is largely maintained, we speak of a conversion of this plan only.

A conversion of such a plan can take place in at least two different ways. A first conversion being the one not specifying any weights using the method of Philipp Suess. A second conversion variant by which a second navigation plan can be generated, being the one using mathematical weights. In a conversion of a starting plan (the first plan), a mathematical weight has the effect that these mathematical weights increase with increasing distance from the initial voxel and the locally defined change is limited to a greater extent in the presence of mathematical weights. The said second navigation plan thus comprises locally defined changes as compared to the first navigation plan. In the first navigation plan calculated without mathematical weights, the changes are spread more widely.

The mathematical weights can be configured such that they are set or specified not uniformly over various directions starting from the initial voxel, but depending on the respective tissue. This is a non-uniform weighting dependent on tissue.

There are two variants of the invention. Both variants use an operating aid, which is called first operating aid and can be, for example, a sliding setting device or a rotary setting device (in brief: slide control or rotary control), wherein inherently not a control but a change is effected. The first operating aid has two end positions, wherein the first end position corresponds to the first plan. This correspondence is such that the position of the setting button of the operating aid determines which plan is illustrated on the display device. When the setting button of the first operating aid is in the first end position, the first plan is illustrated, which is the starting point anyway.

The two variants of the invention now are such that assignment of the second end position of the first operating aid can be effected in various ways.

The second end position can correspond to the converted first plan called "first navigation plan" above. Depending on the position of the setting button (of the operating aid), interpolation is performed or the parameters of an interpolation to be performed are specified by the setting of the operating aid.

A plurality of intermediate positions can be provided in addition to these two said end positions Each intermediate position corresponds to an intermediate plan, wherein this intermediate plan results from an interpolation. The interpolation starts with the first plan and proceeds towards the first navigation plan. The further the operating aid is adjusted towards the first navigation plan, i.e. the second end position, the more the illustration resembles the first navigation plan. In this connection, an interpolation is a temporarily calculated intermediate solution (as an intermediate plan) which is located farther or less far from the first plan and closer or less close to the first navigation plan in terms of content, respectively, corresponding to the position of the button.

Interpolated intermediate plans are not computationally intensive and can be calculated relatively fast and stored in a buffer which makes them again available for an adjusting movement of the operating aid.

In a second variant of the invention, the end value of the first operating aid is a different value. In this variant, this end position is called third navigation plan generated by a conversion of the first plan, taking into account the change in dose in the small/local voxel group and another influence This other influence may be zero so that the end position of the first operating aid corresponds to the first navigation plan. However, this influence can also be exerted differently so that the change corresponds to the second navigation plan. There is a plurality of intermediate plans between these two possibilities, wherein the third navigation plan is generated by way of interpolation from the first and second navigation plans.

All the conversions relate to or take into account the change in dose in the small/local voxel group and are, on principle, based on the first plan. None of these intermediate plans is one of the pre-calculated solutions previously stored in the database, but originate from the first plan and the two navigation plans calculated according to the regulations of Philipp Suess. The conversion into the navigation plans is based on a mathematical description of their targets, i.e. the local improvement in a small voxel group, while making only slight changes elsewhere. The method described by Suess enables a conversion with such a (target) description.

By means of this at least one converted navigation plan and the at least one operating aid, intermediate plans can be generated which enable the user to perform control virtually continuously and to examine, illustrate and evaluate a plurality of intermediate plans as to whether they will adequately achieve the desired target, namely a change in dose in a small group of voxels to be performed as a locally defined change, while substantially (not quite, but very close) maintaining the plan and with substantially the same DVH distribution.

In a third variant, the focus is on the intermediate positions of the at least one operating aid changeable in its setting. An intermediate plan is illustrated on the same display device depending on the changeable setting of the first operating aid. It has two end positions and a plurality of intermediate positions. The first end position still corresponds to the first plan (the initial plan) and each of the intermediate positions corresponds to another intermediate plan. They are obtained from a respective interpolation between the first plan and the navigation plan. One of the interpolated intermediate plans is the causal follow-up plan to be set (later) on the technical device and by which the change in the first plan has been effected in the area of fineness specified in terms of volume.

In the second variant of the invention, the third navigation plan is generated from the said influences and is provided to the first operating aid as an end value or placed there for the user. Depending on the setting of the first operating aid, either the first plan or the third navigation is then illustrated on the same display device depending on the setting of the first operating aid with its at least two end positions. The first end position, usually on the left, corresponds to the first plan. The second end position, usually on the right, corresponds to the mentioned third navigation plan.

Further intermediate positions of the first operating aid may exist between these two end positions, wherein each intermediate position corresponds to an intermediate plan corresponding to an interpolation between the first plan and the third navigation plan. When the operating aid is located closer to the second end position, the illustration corresponds to the third navigation plan. When it is located closer to the first end position, the illustration is closer to the first plan.

The intermediate positions themselves are not required to be incremental but may arise virtually continuously, wherein the length of the operating aid or the angle of rotation of the operating aid plays a part and determines discretization as to how may intermediate plans are to be accommodated on the setting length or setting angle so that the user is given some kind of continuous feeling even though individual interpolated intermediate plans are displayed to him during rotation or sliding.

Within the scope of the second variant of the invention, an additional operating aid can be provided.

By means of the additional operating aid, it may be specified what end value of the first operating aid is set. When the second operating aid is merely a switch, it can be switched between the first navigation plan and the second navigation plan. When the second operating aid is also an actuator, for example, a slide control or a rotary control, a plurality of different plans can be defined as an end value of the first operating aid which plans are, in turn, converted by way of interpolation between the first navigation plan and the second navigation plan. Thus, the third navigation plan is generated as the end value of the first operating aid specified or preset by the position of the second operating aid.

Two sliders (linear setting devices) are illustrated in the embodiments. Rotary controls or even planar actuators, wherein a surface area is defined by the two linear operating aids, for example, in the shape of a triangle, are possible as well. Changes can be made virtually continuously within the surface area of the triangle.

This planar configuration of an operating aid may have two corners of the triangle represent the two end positions of the first operating aid. When the second operating aid, for example in form of a linear length, is arranged perpendicularly to the first operating aid, it forms a triangle therewith by the end points, and a position taken, for example, by a cursor deviating from the straight line of the first operating device (between the first two corners of the triangle) towards the third corner is a measure of how the second operating device changes the end value of the first operating device.

Alternatively, the triangle also works in the specific case that precisely three plans are interpolated. These three plans are associated with the corners and the positioning of the operating aid within the area of the triangle generated by these corners corresponds to an interpolation between these three plans.

This kind of operation may use the three plans are predetermined (specified) irrespective of their origin and interpolation is performed between them.

An improvement in fineness of change aiming only at a locally defined change arises for the user also when using only one operating aid. The user may move within a continuum of plans by positioning the first operating aid or by additionally positioning the second operating aid, if necessary, which plans are all based on the first plan and are interpolated during the movement of the operating elements. Such an interpolation involves that a setting of the first operating aid closer to the first end position corresponds to an intermediate plan which is closer to the first plan. The same applies to the proximity of a setting button of the first operating aid with respect to the second end position, however, in this case, the displayed intermediate plan is closer to the first navigation plan (first variant of the invention) or a mixture of two further navigation plans converted, for example, with and without mathematical weight, or the second end position corresponds to the second navigation plan when this is specified by a second operating device and the second operating device can effect changes between the first and the second navigation plan or a mixture thereof. This mixture corresponds to the said other influence on the third navigation plan which is conceptually addressed in the second variant by the end of the first operating device and is illustrated on the display means.

For example, a computation can be used as an interpolation calculating an intermediate plan from the first plan depending on the position of the setting button of the first operating aid, which intermediate plan is located between the first plan and the first navigation plan. This interpolation can equally be performed also between the first and second navigation plans, wherein the first navigation plan is converted without mathematical weights and the second navigation plan is calculated with mathematical weights from the first plan using the calculation regulation of Suess and changing this interpolation further towards the first navigation plan or further towards the second navigation depending on the position of the second operating aid in order to define the third navigation plan which will become the end value of the first operating aid.

The interpolation can be configured as follows.

Interpolation is the generation of a usually transient intermediate plan from existing navigation plans. According to its name, this interpolated intermediate plan is located between the plans used for generation thereof.

The most widely used method is the so-called convex combination. Here, a number of initial plans with associated weights are mixed in accordance with the weights. The weights sum up to 100% in the process. The mixing is applied to fluences of the plans (physical plan parameters). Since the radiation dose (in very good approximation) is linearly dependent on the fluences, the dose distributions of the plans can be added in a weighted manner analogous to the fluences.

However, as the fluences are not the settings of the irradiation device, but since the leaf settings of the multi-leaf collimator with associated times are primary quantities, the fluences (which are theoretically mentioned for this reason) are converted into such leaf settings in a process called "sequencing". The conversion of the device settings is thus not performed by convex combination.

Apart from convex combination, somewhat more complicated interpolation mechanisms would also be possible. For example, the plans could also be scaled.

The interpolation parameters (e.g. what plans, what weights) can be read directly from the position of the operating aid or can be indirectly derived from the position. A quality value (not a parameter value!) is set by the position of the operating aid and, in a very small optimization problem, the interpolation parameters are determined such that the values of the other axes are changed as little as possible. This problem is so small that it can be solved in real time so that the user will not be aware of the interpolation.

It is understood that the central position of the operating aid causes the display of, in brief: displays, such an intermediate plan on the display means being interpolated between the first plan and the first navigation plan (first variant of the invention) or the third navigation plan (second variant of the invention), wherein the third navigation plan can be the first one, the second once or a mixture thereof.

It is again pointed out that the plans are not pure information, but technical data and thus correspond to dose distributions set in the technical device for tumor therapy.

It is virtually impossible to describe these technical device settings in a patent claim in a manner intelligible for the user without reference to a representation comprehensible to the viewer. A column of irradiation intensities, irradiation times and associated angle information is not a perceptible or assessable device setting to a user. It is a purely technical setting calculated or computed by a higher authority, which higher authority is conceivably associated with the therapy plan to the viewer. Such as the sections including the isodose lines which constitute examples or a DVH diagram providing useful, but not sufficient representation of the entire plan in an image as a standard of evaluation.

The interpolated intermediate plans generated during movement of the operating aid (the first or second operating aid) are not stored in the database. They are temporary intermediate plans which are not pre-calculated plans. They are too similar to these pre-calculated plans. However, they are stored in a buffer to be exported when needed, i.e. when favored by the user who approves of this interpolated plan for his purposes, and to be provided for the device settings. This exported plan is the causal follow-up plan to be generated or determined, for which purpose the above defined steps of the invention are performed. In this sense, a data base is also memory but not the memory for which the interpolated (volatile) plans are provided.

Operating aids, cursors and rotary controls or slide controls have been spoken of before. They are not necessarily to be understood as tangible rotary adjusters in a physical sense, such as for example a potentiometer or slider. In application, these representations are, in most cases, displayed optically on a monitor and can be displayed on a separate display device, while the other display device displays the plans, for example, in form of a DVH diagram and three sectional diagrams with isodose lines (transverse, sagittal and frontal).

Further display quantities representing additional similarities or other values of change can additionally be provided which can be accommodated either on the first or second display device.

If desired, the first or/and second operating aid can also be implemented physically and provided in form of tangible potentiometers to the user who will then change the plan on the monitor by physical rotation or sliding (without using a pointing device with cursor). The implementation via an AD converter or incremental potentiometer having discrete positions are only two of a variety of possibilities of making operational guidance of the system as easy and practically convenient as possible for the user.

A setting button can effectively be represented graphically directly on a display device and operated by a pointer of a controller (a mouse device) or can be implemented physically and provided in tangible form to be touched by the user.

BRIEF DESCRIPTION OF THE DRAWINGS

Embodiments of the invention are explained in greater detail on the basis of Figures. An overview is given for this purpose.

FIG. 1 is a block diagram of a control arrangement with two display devices 110, FIG. 2 symbolically shows the plan volume Z illustrated in following FIG. 4.

FIG. 3 is a DVH diagram 70.

DETAILED DESCRIPTION OF THE DRAWINGS

Figure 4A:
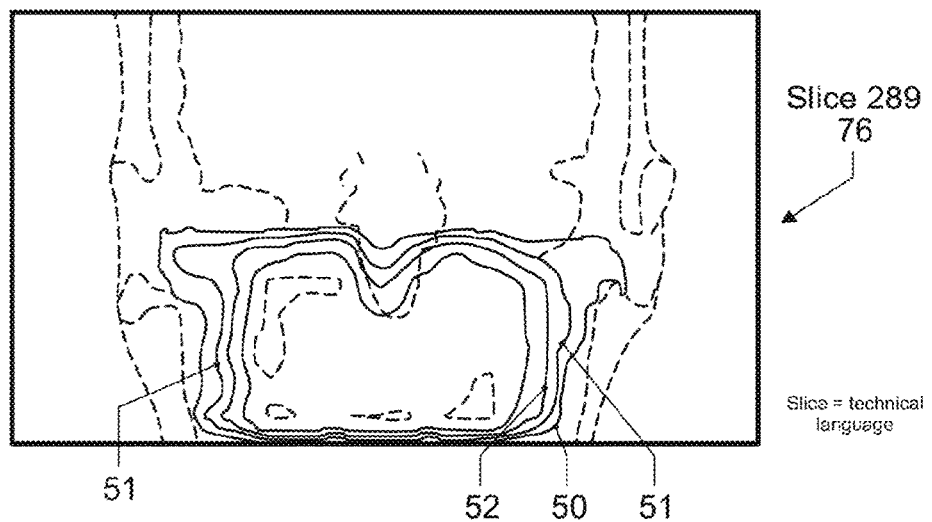
FIG. 4a, FIG. 4b and FIG. 4c each illustrate a sectional plane (slice) in three spatial directions.

FIG. 1 is a block diagram of a control arrangement with two display devices 110, 111. 100 is a database and 150 a central control and calculation core having a buffer 120 used for storage and buffering of interpolated plans.

FIG. 2 symbolically shows the plan volume Z illustrated in following FIG. 4. A plane is illustrated here of which a plurality of planes exists which are denoted by $y_1$ to $y_n$, wherein the initial voxel z1 comes to lie in plane $y_i$, as selected later and explained later. Z represents the plan volume Z divided into a plurality of layers in three spatial directions for calculation and illustration, within which plan volume the locally defined volume z is located illustrating the area of fineness specified in terms of volume with its boundary 10a.

FIG. 3 is a DVH diagram 70 showing the volume percentage on the vertical axis and a dose scale between 0 gy and 100 gy. Plotted as characteristics are both, the target volume (first and second tumor, at the far right, reference numerals 80 and 81) and characteristics (curves) of risks explained in greater detail in the following.

Figure 4B:
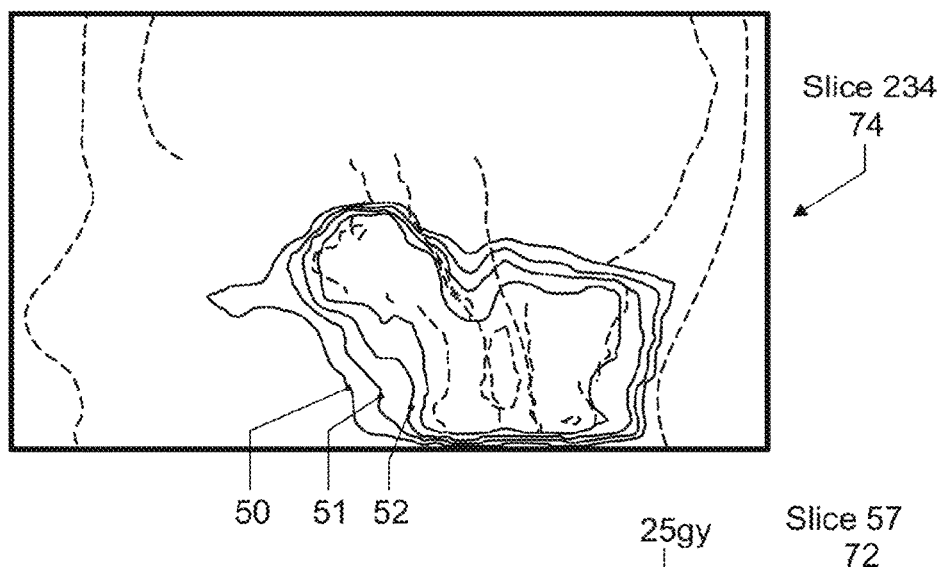
Figure 4C:
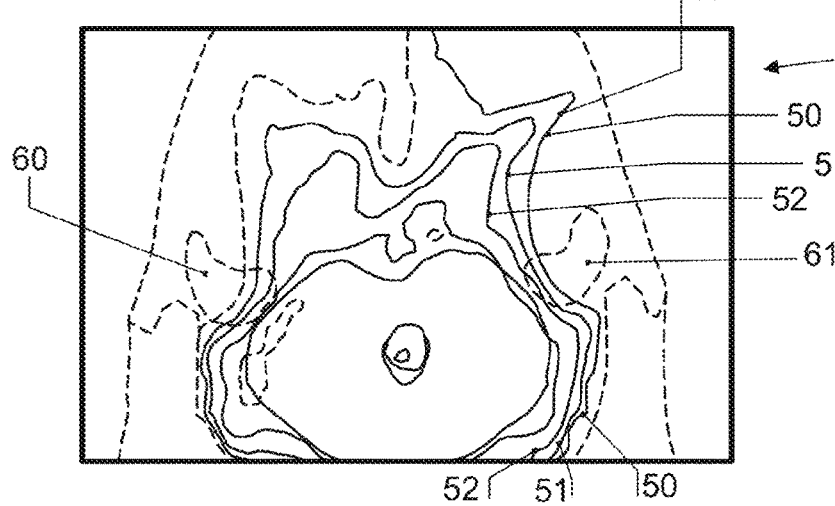

FIG. 4a, FIG. 4b and FIG. 4c each illustrate a sectional plane (slice) in three spatial directions, wherein FIG. 4a shows sectional plane 289 of the frontal sections, FIG. 4b shows sectional plane 234 of the sagittal representation, and FIG. 4c shows sectional plane 57 of the transverse sectional planes. The sectional planes are often also called "slice", wherein the plane volume is divided in three spatial directions into a specific number of slices per spatial direction, and wherein isodose lines are defined within a respective slice similar to the contour lines of a mountain range, said isodose lines characterizing lines of equal dose. For example, a gradation of doses of 25 gy, 33 gy, 40 gy, 50 gy, 60 gy and 65 gy, i.e. six grades of doses, is illustrated in FIG. 4c. In an illustrative example, the outer line is the isodose line of 25 gy and two organs 60, 61 are spatially represented which constitute the left and right parotid glands on the left and on the right in the shape of kidneys. Isodose lines 50, 51, 52 denote three external isodose lines in the examples.

Figure 5:
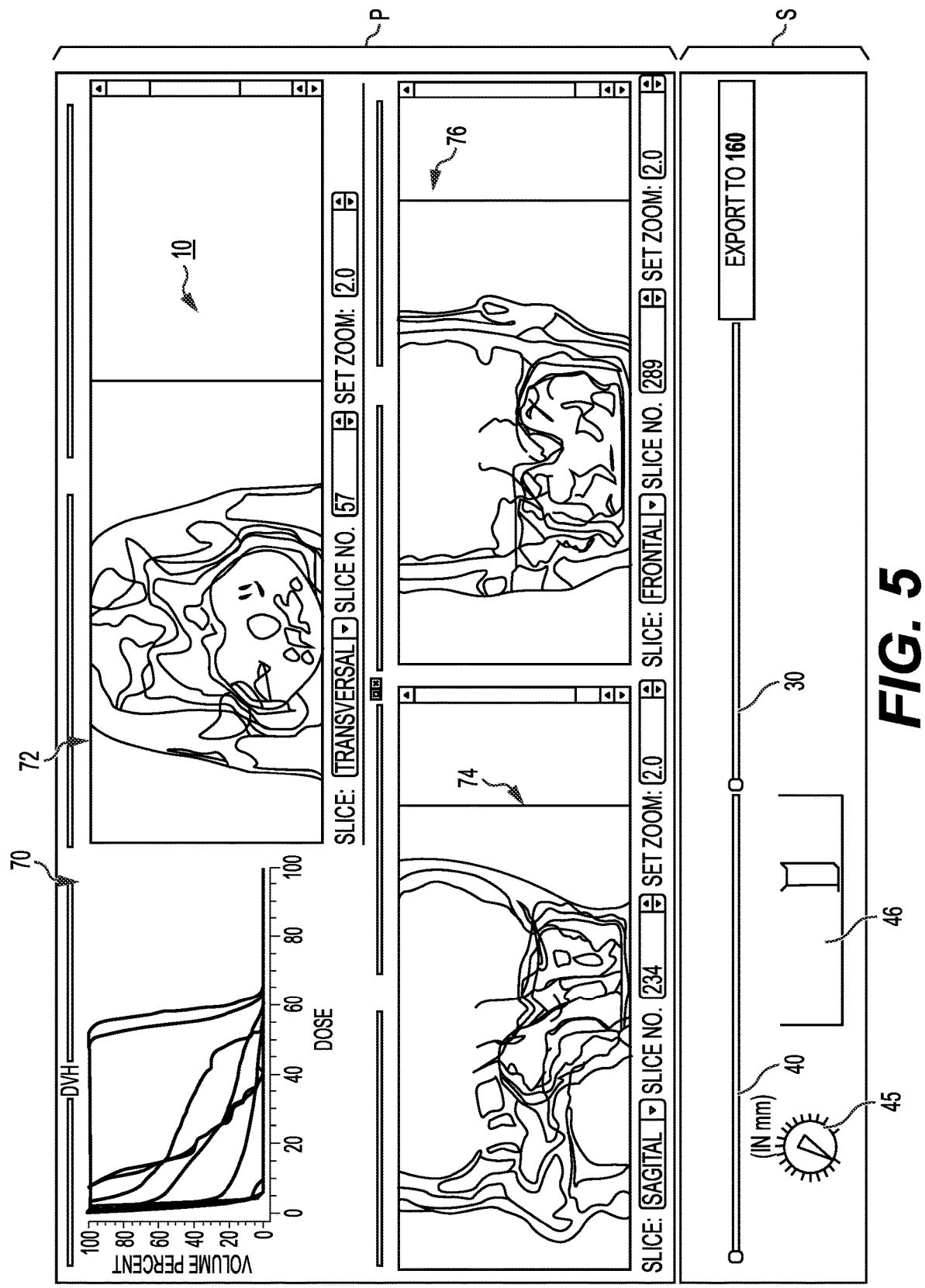
FIG. 5 is a summary of the individual illustrations of FIGS. 3, 4a, 4b, 4c and their partial images 70, 72, 74, 76 with added operating aids 30, 40.

FIG. 5 is a summary of the individual illustrations of FIGS. 3, 4a, 4b, 4c and their partial images 70, 72, 74, 76 with added operating aids 30, 40. The four illustrations consisting of a DVH diagram and three sectional planes of isodose lines represent "a plan".

A plurality of characteristics of organs, tissue areas and target volumes are shown in partial image 70 of FIG. 5. The two right-hand characteristics are two target volumes (tumor volumes). The central curve with the long slope represents the brain stem. The two steeper characteristics extending substantially in parallel represent the left and right parotid glands. The more level curve extending roughly parallel to the characteristic of the brain stem in the central portion is the body. The curve approximated to a 1/x function is the dose characteristic for the entire brain and the residual steeply sloping curves are risk organs (optics, left and right eye).

The operating aids 30, 40 in setting section S can be seen on the same display device, for example 110 of FIG. 1, together with the plan representation. The lower section S comprising the setting aids could also be placed on the display device 111 so that only section P remains on the display device 110 for representation of the set plan. Setting section S could also be realized in hardware, e.g. by two external setting controls which can be operated manually, such as 130, 140 of FIG. 1. FIG. 5 represents the first plan 10 which is also a representative of a variety of technical setting parameters of the non-illustrated device TG for tumor therapy, cf. e.g. U.S. Pat. No. 6,038,283 A (Carol et al, Nomos), FIG. 1 therein.

Figure 6:
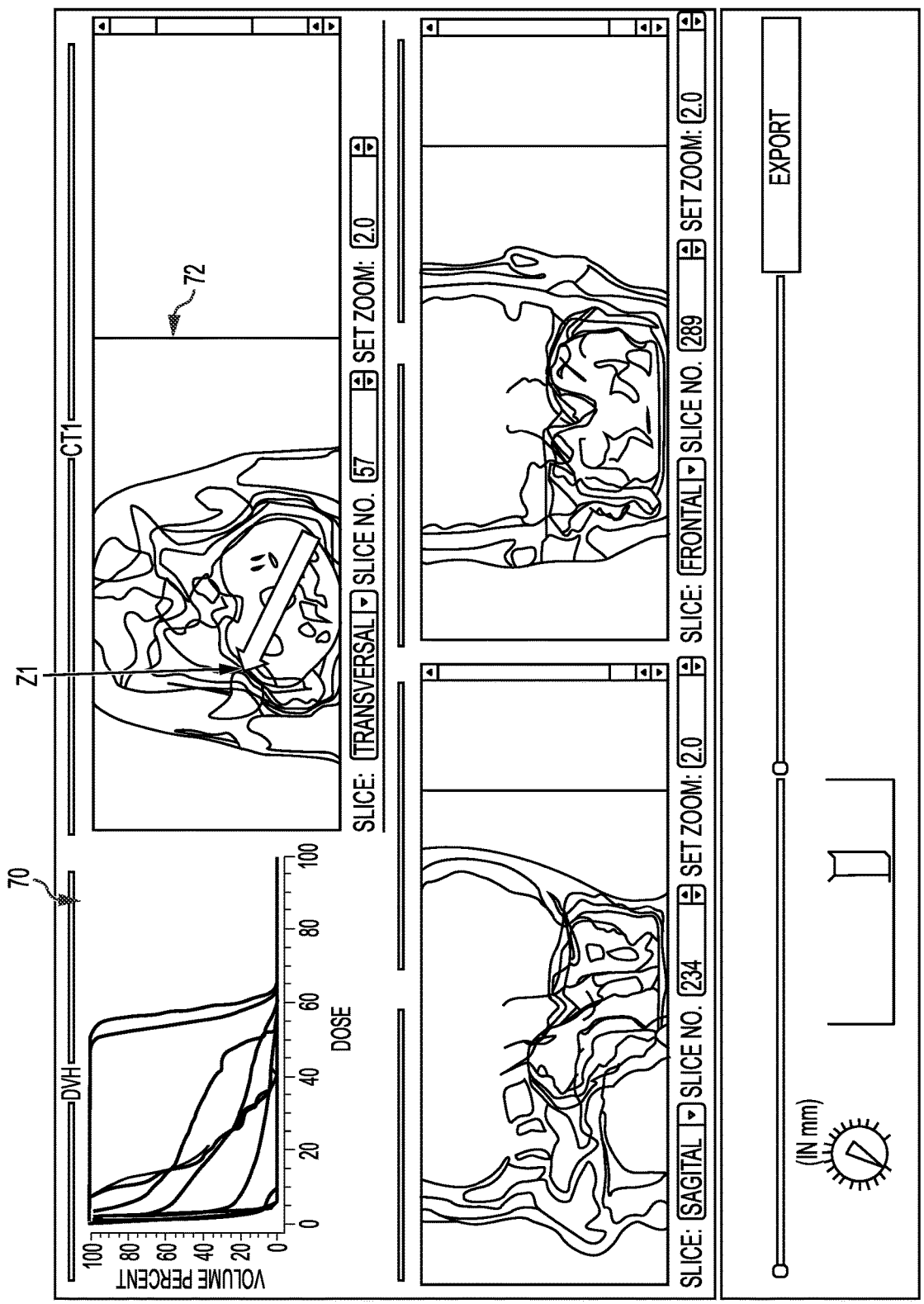
FIG. 6 shows the selection of an initial voxel z1.

FIG. 6 shows the selection of an initial voxel z1. This voxel is located in level 57 of the transverse sections (top right diagram). The other representations are unchanged as compared to FIG. 5, since only one selecting action has taken place using a mouse pointer.

Figure 7:
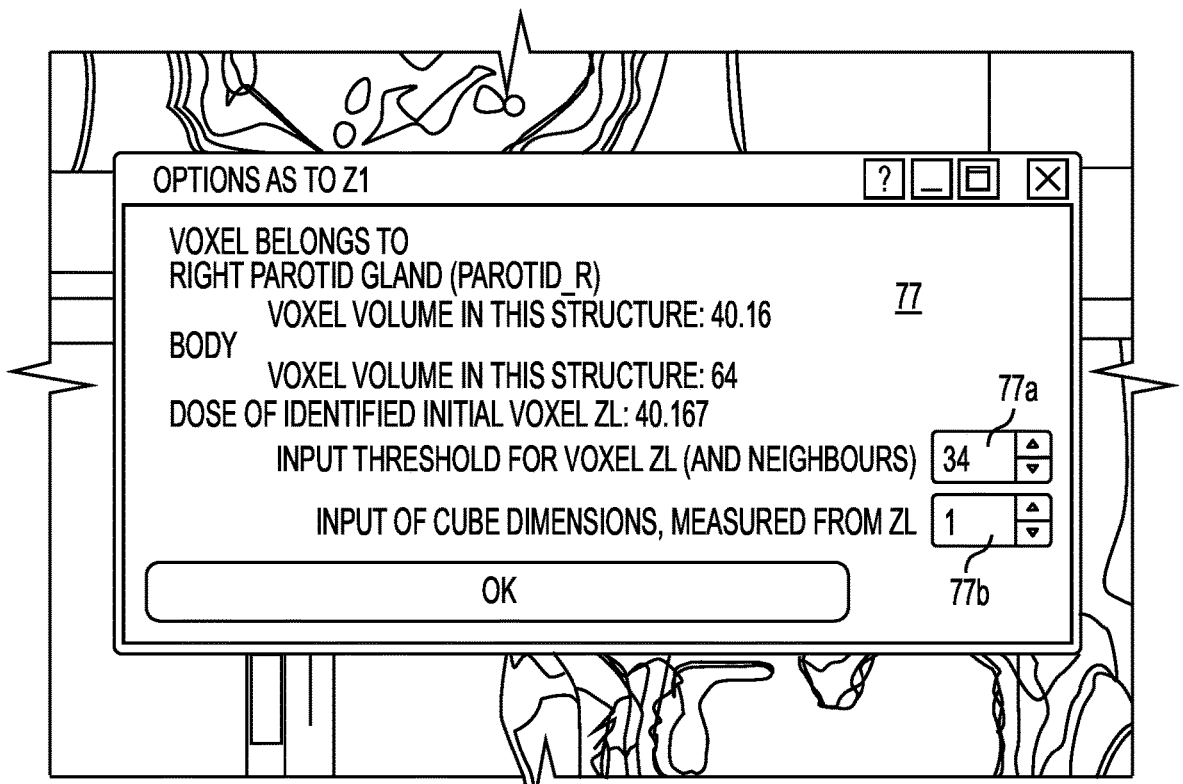
FIG. 7 shows the dose value at the selected point z1 of FIG. 6 in a displayed window 77.

FIG. 7 shows the dose value at the selected point z1 of FIG. 6 in a displayed window 77 including information on the initial voxel and setting options regarding the size of the area of fineness specified in terms of volume and the desired dose.

Figure 8:
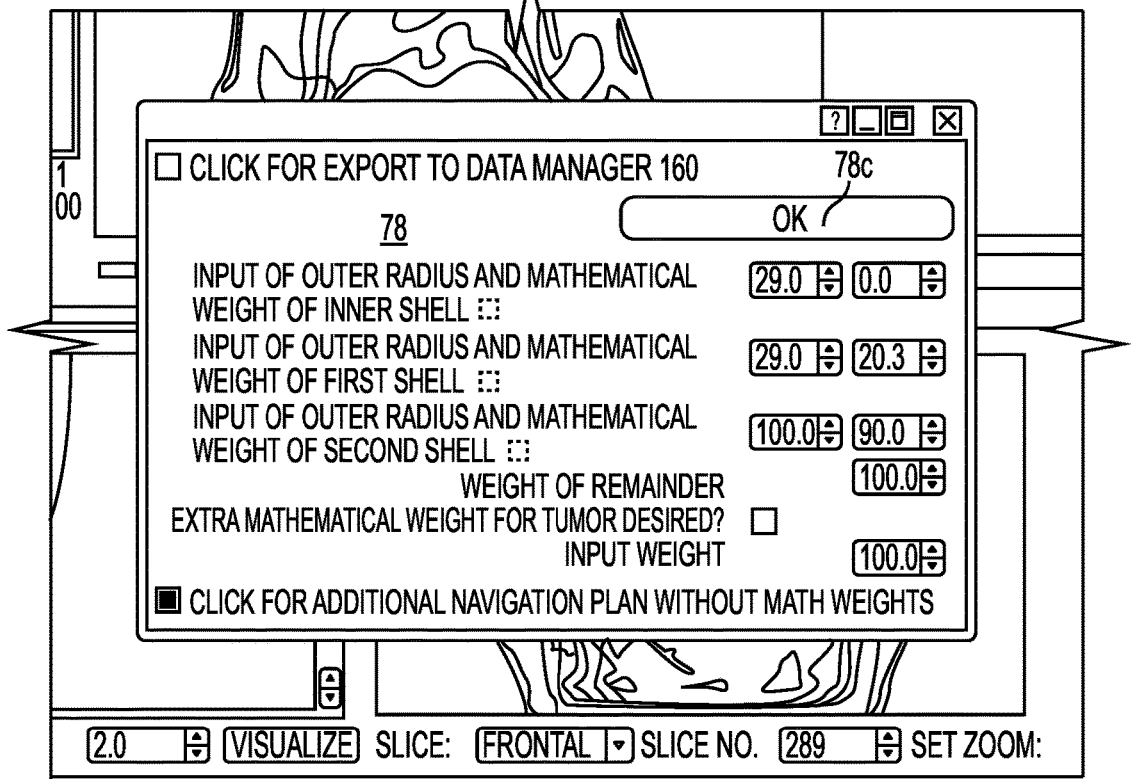
FIG. 8 shows a further window 78 displayed after confirmation of the window of FIG. 7.

FIG. 8 shows a further window 78 displayed after confirmation of the window of FIG. 7. Here, the parameters of conversion are set, by which the first and second navigation plans are generated or converted from the first plan illustrated in FIG. 5.

Figure 9:
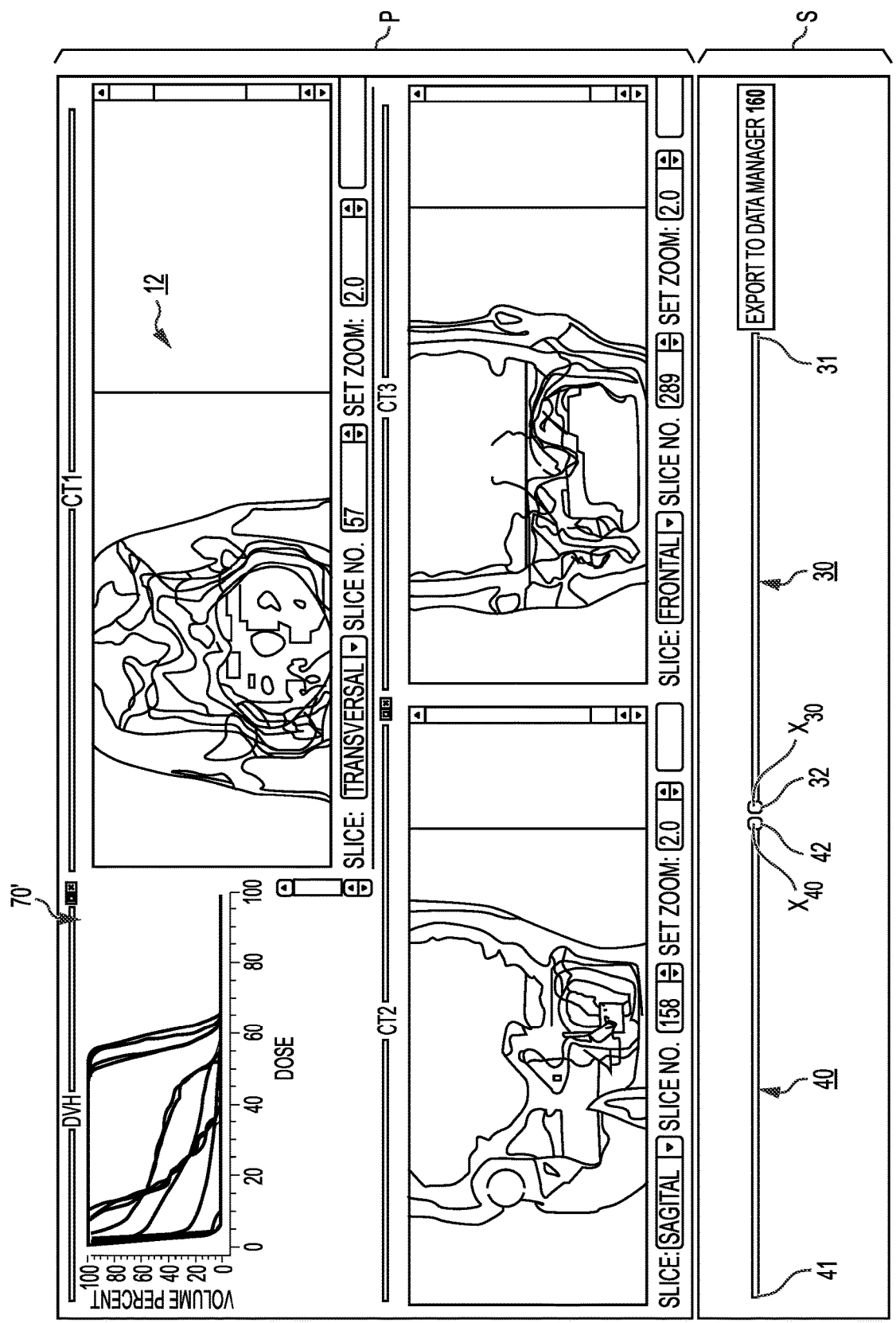
FIG. 9 shows activated operating aids 30, 40 which are activated subsequent to the presence of a first navigation plan and/or a second navigation plan.

FIG. 9 shows activated operating aids 30, 40 which are activated subsequent to the presence of a first navigation plan and/or a second navigation plan. The setting buttons X40 and X30 of the two operating aids represented as sliders 40, 30 are displaceable between the left and the right and also include intermediate positions. Each one of the "sliders" has a left and a right stop called end stop or end position. The end stops 41, 42 of operating aid 40 and end stops 31, 32 of operating aid 30 are represented in FIG. 9. The second navigation plan 12 is represented in the upper plan section P of the display device, which could also be completely identical with 110 of FIG. 1, while the setting section S could also be placed on the second display device 111, however, in the image of FIG. 9 both sections are provided on one display device.

Figure 10:
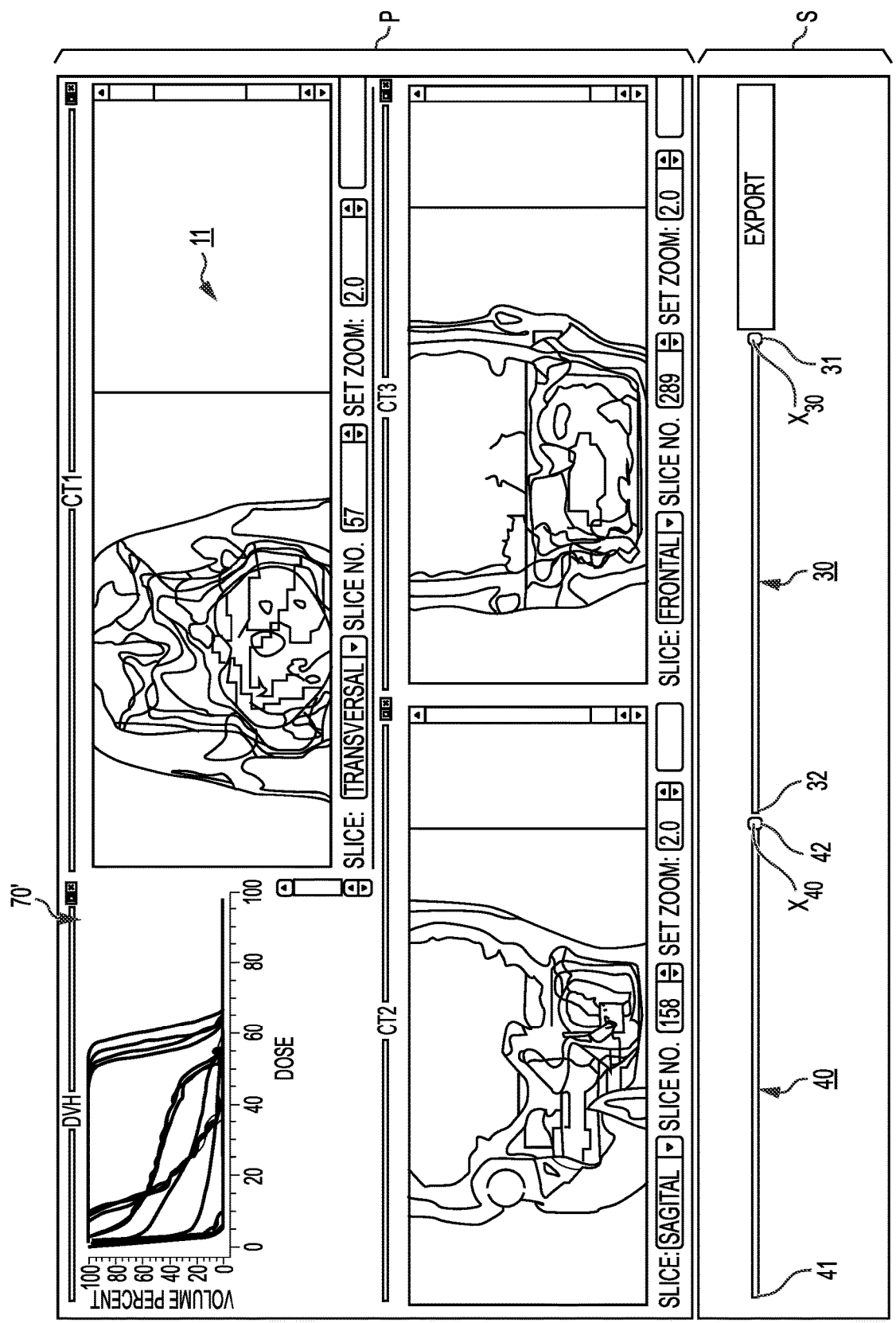
FIG. 10 shows a representation corresponding to FIG. 9.

FIG. 10 shows a representation corresponding to FIG. 9, however, in this case, the first navigation plan 11 is illustrated in plan section P. This is due to the setting of slide buttons X30, X40 of the two operating aids 30, 40, as explained in greater detail in the following.

Figure 11:
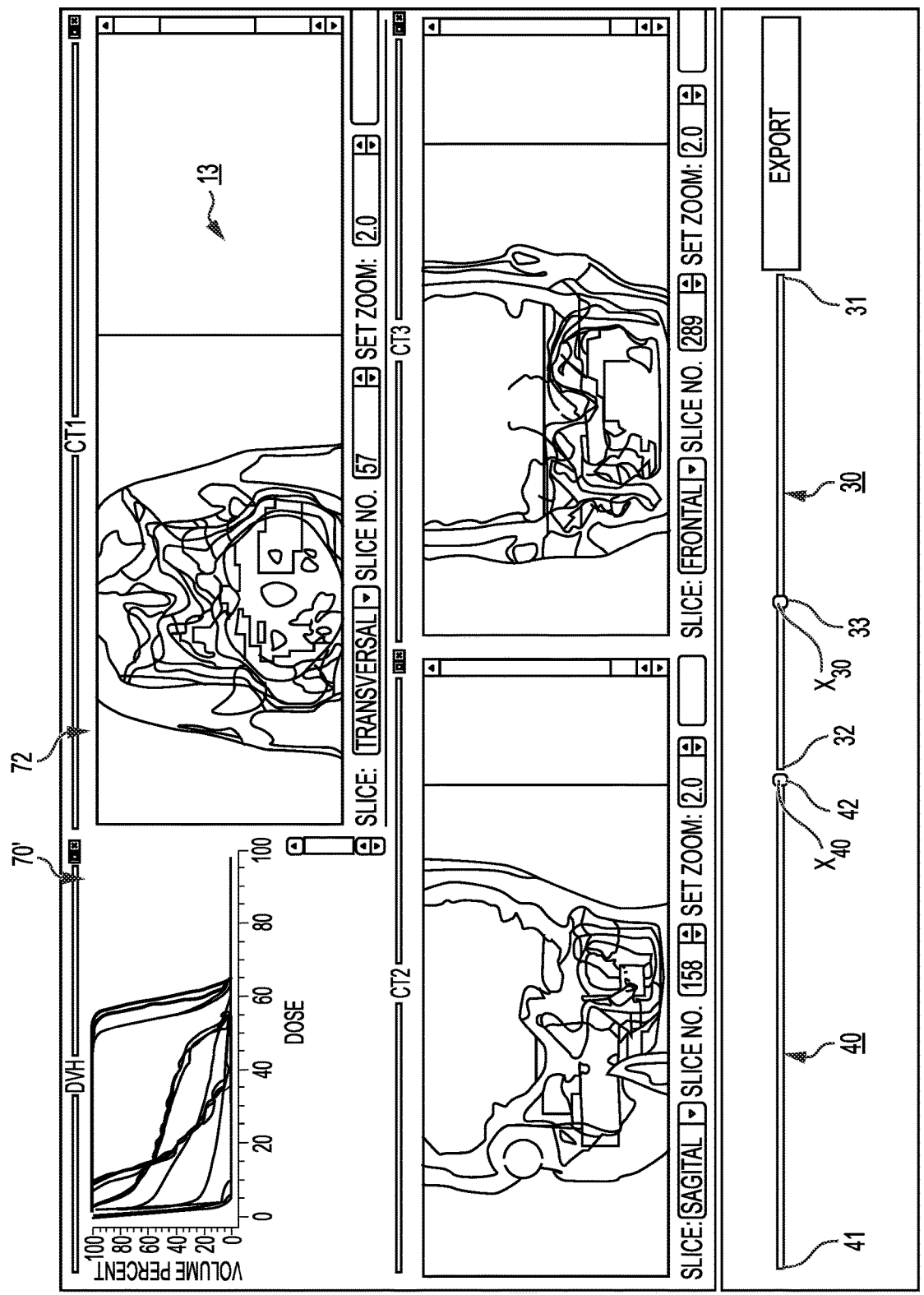
FIG. 11 illustrates another setting of operating aids 30, 40.

FIG. 11 illustrates another setting of the operating aids 30, 40. Here, the first operating aid 40 shown on the left is located at its right stop 42 and illustrates the plan in plan section P as specified by the right operating aid 30. The setting button X30 thereof is located in an intermediate area at position 33 and represents an intermediate plan between positions 31 and 32 representing an interpolation between the first navigation plan 11 selected at position 31 and the second navigation plan 12 selected at position 32. A third navigation plan 13 results at position 33 specifying the end value of the first operating aid 40, and when the setting button X40 thereof is placed at the second end position, as shown in FIG. 11, the third navigation plan 13 is illustrated in plan section P.

Figure 12:
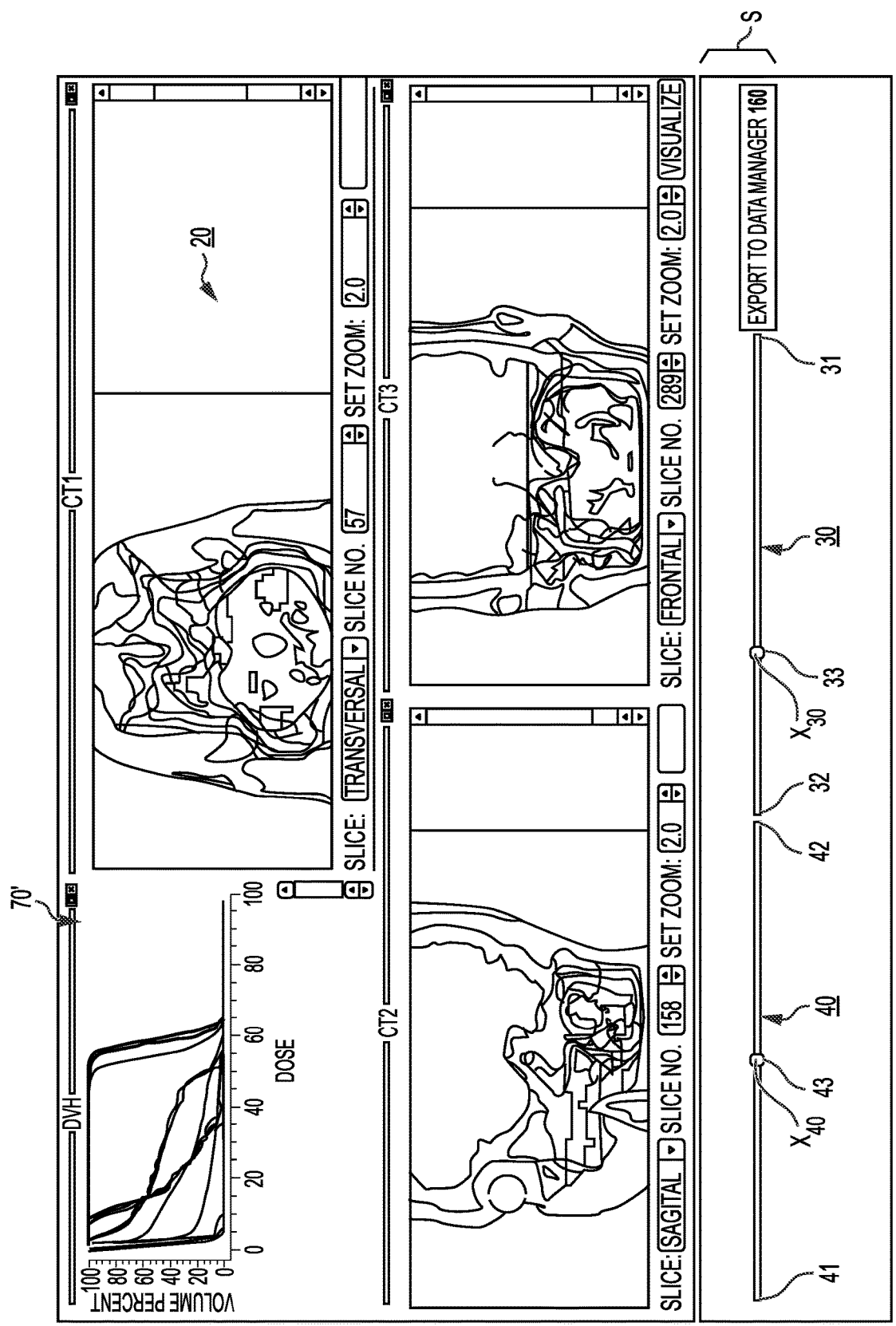
FIG. 12 illustrates the generation of the causal follow-up plan 20.

FIG. 12 illustrates the generation of causal follow-up plan 20 as accomplished by intermediate positions 33, 43 of the first and second operating aids 40, 30 which are interpolated in each case, as explained in greater detail further below.

Figure 13:
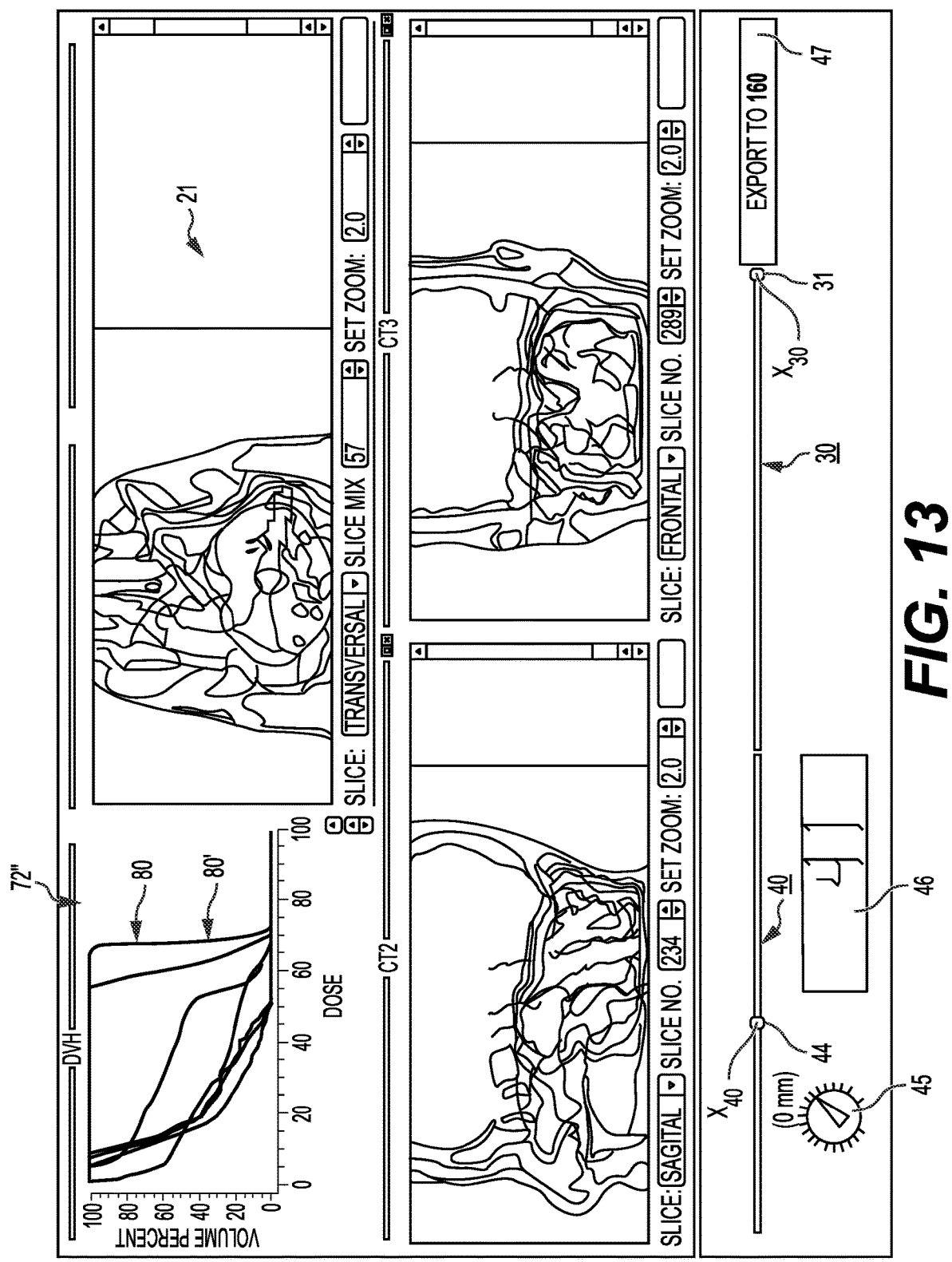
FIG. 13 illustrates the generation of a further causal follow-up plan 21.

FIG. 13 illustrates the generation of a further causal follow-up plan 21 as accomplished by different intermediate positions of the first and second operating aids 40, 30 which are interpolated in each case, as explained in greater detail further below.

Figure 14:
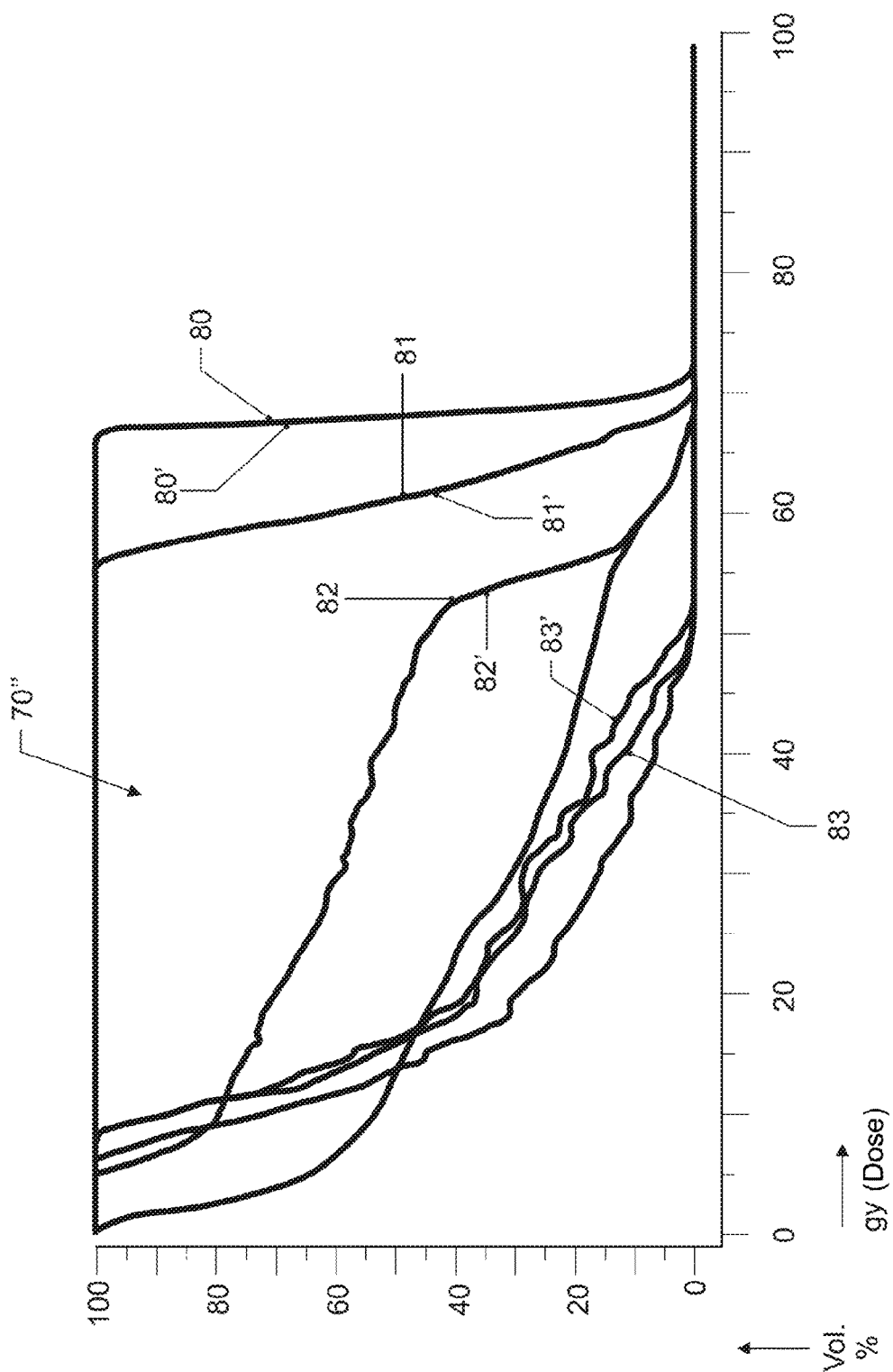
FIG. 14 illustrates a DVH diagram 70".

FIG. 14 illustrates a DVH diagram 70" representing both plans, the first plan 10 and the causal follow-up plan 21 of FIG. 13 in one image illustrated in two views. Only a few curves are chosen as characteristics, but are always illustrated in pairs, e.g. the tumor area represented by characteristics 80 and 80'.

In the above extended overview of the Figures, one plan is illustrated in plan section P in each case. In the example, this plan consists of four representations 70 to 76 explained in connection with FIGS. 3, 4a, 4b and 4c. They comprise one DVH diagram 70 and three sectional diagrams wherein, for each image (segment), the sectional plane or slice number is indicated, which number has been kept consistently identical for the sake of explanation.

The transverse section is slice 57, the sagittal section is slice 158 and the frontal section is slice 258. This applies to all Figures in order to enable a comparison between all images of the isodose lines in the representations of cutout images 72, 74 and 76 and the isodose representation of image 70.

In the representations of the plan section or plan sections of FIGS. 9 to 13, the image 70 of the DVH representation of FIG. 3 is used twice in order to illustrate the original plan 10 (located at the starting position 41 of the first operating aid 40) and the new, changed plan accomplished by changing the position of setting button X40 and/or X30.

A further curve representing the change has been additionally provided for each curve of FIG. 3 in DVH image 70', however, it is also apparent that this change is so slight that the original plan 10 (the starting plan) of FIG. 5 is virtually still present, however, includes a new stipulation made on the basis of FIG. 6 and the setting of FIGS. 7, 8.

An overview on the circuit structure and the components of the system for finding a causal follow-up plan, by which a setting of the technical device or on the technical device for tumor therapy is performed, is shown in FIG. 1.

FIG. 1 is to be read in conjunction with FIG. 5, since the display device 110 of FIG. 1 visually illustrates at least plan section P of FIG. 5 to the user. The individual segments 70, 72, 74, 76 are apparent from FIGS. 3, 4a, 4b and 4c and are explained in greater detail therein. They represent a plan which, in the image of FIG. 5, is the first plan 10 originating from a previously stored amount of pre-calculated plans in the database 100.

The setting portion S of FIG. 5, which, in contrast to plan section P, is illustrated below this plan section in FIG. 5, may also be placed separately on a further display device 111 which can also be a monitor. However, a mechanical actuator can also be used and the operating aids 30, 40 of FIG. 5 are represented as mechanical actuators, in form of a potentiometer 130 or slide control 140, in FIG. 1. They constitute an alternative to the optically displayed actuators, e.g. sliders 30, 40, as an English-language synonym to slide controls.

The operating aids 30, 40 or 130, 140 are used by a non-illustrated user to change the representation on the screen as an example of a display device 110. He intends to change a fine area specified in terms of volume, the volume boundary of which is represented by 10a in FIG. 2. The plan volume Z is also schematically shown in FIG. 2 which emerges more realistically from FIG. 5.

For this purpose, the setting aids 30, 40 are moved between their end positions 31 and 32 as well as 41 and 42. This can be correspondingly performed by the haptic touch adjusters which are shifted by manual touch. A touch screen is a further variant.

The central control core 150 couples the said components in terms of function and data. It accesses the database 100, operates the display device 110, and possibly 111, via a video interface, receives signals from the operating aids 30, 40 or 130, 140 and comprises a buffer 120 in which the interpolated intermediate plans can be stored and retrieved therefrom.

The normal case of the coupling 100a between the database 100 and the central control core 150 is that 150 retrieves a first plan 10 from the database and illustrates it on the display device 110. Usually, it is not intended to restore this plan or further plans in the database 100 and the plans converted by the central calculation core 150—also having a control function—are stored in the temporary memory 120.

When a causal follow-up plan 20 has been generated from the initial plan (the first plan 10) on the basis of the mode of operation of the system and the user guidance, this follow-up plan can be transmitted at the touch of a button, e.g. by using the button 47 of FIG. 12, to the data manager 160 and can be buffered therein. This buffering is converted into setting parameters supplied to the technical device TG by a technical interface 161 not illustrated in greater detail. Possible technical setting parameters include time periods, intensities, specifications for multi-leaf collimators, or angle settings for a radiation head which can be rotationally moved about the patient. The setting types of TG are known, the devices TG are known as well so that only the interface 161 is to be adapted to the known setting options. However, what settings are made is a matter of the examples of this description.

In order to place the object and result of this operating principle of FIG. 1 or the system of FIG. 1 operable in the described manner up front, it is referred to FIG. 12.

The arrangement of the individual images 70', 72, 74, 76 and of the setting devices 30, 40 of FIG. 12 is comparable, however, a different plan 20 is illustrated which is accomplished on the basis of different settings of the sliders 30, 40. After actuating button 47, this plan 20 is transmitted to the data manager 160 and supplied to the technical device TG via interface 161.

FIG. 2 illustrates the plan volume Z and the external envelope 10a of the small local area of fineness z determined by selection of the initial voxel z1. In the schematic image, slice y is the one having number 57 so that, in slices $y_1$ to $y_n$, slice $y_{57}$ contains the initial voxel. This selection is shown in FIG. 6, wherein the mouse pointer points to the initial voxel z1 in the right top partial image 72 in the region of the right parotid gland 60. FIG. 2 schematically represents nothing else, only in side view and not in top view.

The user has selected this position z1 on the basis of his experience, desires or targets and wishes to locally reduce the dose at this point showing a relatively high dose while substantially maintaining the residual plan represented by the DVH diagram in the left top partial image 70.

The user could also have identified the initial voxel z1 in the same way in any one of the other sectional views of FIG. 6. In terms of result, a follow-up image of FIG. 7 is displayed when selecting the initial voxel z1 in one of the three isodose representations 72, 74, 76 as partial images of FIG. 6. This is done by means of the display device 110 or a parallel display device 111.

The pop-up window 77 provides more detailed information on the "clicked on" initial voxel z1 (identified by pointing/clicking with a cursor). The available setting "options" in window 77 are specified in setting fields. The dose of the voxel is indicated, the location of this voxel (right parotid gland) is indicated and two values can be specified which can be input in setting fields 77a, 77b by the user. The user can define the size of a voxel group corresponding to the volume z. In the example, this has been done by inputting half an edge length of a cube containing the clicked on voxel. This is entered in field 77b. The user can input a desired dose in field 77a which is to be applicable to the entire voxel group z. In the example, a value of 34 has been input. Thus, the aim is to reduce the dose from 40 gy to 34 gy.

In the example, release of this specification is effected by actuating the button 77c. After release, which corresponds to a desired change in dose and defines a volume within which this change is to take place, the follow-up window 78 appears.

The further window 78 appears in FIG. 8 wherein a plurality of other parameters can be set. These parameters determine the conversion which is to take place starting from the first plan 10. Conversion is performed using the process regulation of Philipp Suess, as cited at the beginning. Mathematical weights are set which are initially suggested by a presetting. The presettings are apparent from the image and relate to spherical shells and weights. The weights increase with increasing distance from the initial voxel and enhance the degree of localization in conversion.

The field 78 may appear once, twice or a number of times.

When it appears a second time, different mathematical weights can be used for calculation, for example no such weights.

It is also possible to perform two conversions using two considerably different weights which result from a first plan 10 in a first navigation plan 11 or in a second navigation plan 12. Usually, the user obtains greatest difference of these two navigation plans 11, 12 when the first navigation plan is calculated without using mathematical weights and the second navigation plan is calculated by using the set mathematical weights.

Confirmation on the confirmation field 78c starts the conversion.

The object of the conversion is the change in dose in the locally defined volume z with the envelope 10a. The initial volume is located within this small volume. In the example, a reduction from 40 gy to 23 gy is to be realized.

In a variant of the calculation, the small voxel group z can be examined by the system as to whether it comprises voxels from the risk area when removing a critical spot from the target area or voxels from the target area when removing a critical spot from the risk area. The number of voxels in the voxel group is 500 at the maximum, preferably less than 350, or, when measured by percentage, not exceeding 5% of the set voxels of the plan volume. The system can reduce the number of voxels to be converted by the voxels associated with the respective other area so that the number of voxels in the voxel group decreases. As an explanation, it can be said that the voxels of the respective other area are not relevant for the removal of a critical spot from an area, i.e. a risk area or target area.

As a result of the conversion according to FIGS. 7 and 8, at least one slider 40 is functionally available as an example of an operating aid in FIG. 9. It constitutes the "first operating aid". A setting button X40 can be moved between the left edge 41 and the right edge 42 of the slider. In the example of FIG. 9, X40 is located at the right edge. Setting button X40 then selects an intermediate plan assigned to this (intermediate) position of the slider 40.

In one embodiment, this may be the second navigation plan 12. However, it may also be the first navigation plan 11. This example is illustrated in FIG. 10.

In both Figures, an additional variant is incorporated which is enabled by use of a second operating aid 30. This operating aid 30 places the first navigation plan 11 and the second navigation 12, respectively, on its two end positions. The position of the second setting button X30 selects what intermediate plan is assigned to the right end position 42 of the first setting aid 40.

By FIG. 8, actually by applying the conversion according to FIG. 8 twice using different mathematical weights, two navigation plans have been calculated which are designated by 11 and 12.

Assuming that the first navigation plan has been calculated without using weights, it is located at the right end position 31 of the second operating aid 30 implemented as a slider in the example. The second navigation plan 12 which has been calculated using mathematical weights is located at the left end position 32. Based on the position of button X30 at the left edge of the second slider 30, the second navigation plan using the mathematical weights is selected and assigned to the right end position 42 of the first slider 40. When the setting button X40 is located here, the second navigation plan 12 represented by the previously addressed four partial images in the example is illustrated in plan section P.

It is apparent that the partial images differ from the initial images of FIGS. 4a, 4b and 4c in intensity by different gray levels. Due to the use of the mathematical weights in the second navigation plan, the changes in plan are more local. This is apparent from a comparison with FIG. 10.

In FIG. 10, a setting has been selected by the two operating aids, wherein the first navigation plan is assigned to the right end position of the operating aid 40, since the setting button X30 of the first operating aid 30 is located at its right stop 31 which is representative of the first navigation plan 11 which has been calculated without using mathematical weights. Consequently, the first navigation plan 11 is illustrated in plan section P.

A word to the DVH diagrams 70' of FIGS. 9 and 10. A pair of curve progressions for an object or area in the plan volume is illustrated in each case, i.e. the first and second tumor, the left and right thyroid glands and several other organs for which there are DVH characteristics calculated by the system of FIG. 1.

A respective pair of curves shows the difference between the original starting plan 10 of FIG. 5 and the causal follow-up plan newly found via the sliders 30, 40 which can only correspond to the first navigation plan 11 or the second navigation plan 12—without mixtures thereof.

From an assessment of the partial image 70' of the two FIGS. 10 and 11 a user may detect that the dose in the target area, i.e. the tumor, (the right curves 80, 81 in the DVH diagram 70 of FIG. 3 and 70' of FIGS. 10/11) has decreased, when using the mathematical weights, i.e. the second navigation plan.

Without these mathematical weights and thus with the first navigation plan 11, a considerable increase in dose arises for the target volume as the tumor. This opens up a further setting option for the user, namely navigation with the second slider 30 between the first and second navigation plans 11/12 by way of interpolation.

This is illustrated in FIG. 11. FIG. 11 shows a position of the setting button X30 between the two end positions 31, 32. This intermediate position is denoted by 33. Here, a third navigation plan 13 arises, which is assigned to the right end position 42 of the first operating aid 40 according to the explanations made to FIGS. 9 and 10. Setting button X40 is also located here so that its setting makes the third navigation plan, according to the setting position 33, appear on plan section P. The third navigation plan 13 has been generated by interpolation between navigation plans 11 and 12 in accordance with the position of the setting button X40 and its spacing from the left and right end positions.

The DVH diagram 70' in the left top partial image shows a clear improvement. The user is provided with a causal follow-up plan which he may generate by shifting the setting button of each of the two operating aids 30, 40 or 130, 140 in an almost continuous manner. For this purpose, not only the two end positions of each of the operating aids, but also one or a plurality of intermediate positions are provided in each operating aid, wherein one intermediate position 33 thereof has been explained with respect to FIG. 11. Further such intermediate positions define further interpolations between the respective end values of one of the operating aids, i.e. both 30 and 40.

The first plan 10 is located at the left end of the left operating aid 40. FIG. 12 shows that also in this case an interpolation between this first plan 10 and the (navigation) plan located at the end stop 42 is possible. This plan is specified by the right operating aid 30 by setting an intermediate value.

The right slider enables interpolation between the first and second navigation plans, provides an interpolated plan at position 33 (by the location of setting button X30 as the third navigation plan 13) and the left slider 40 interpolates the mentioned mixed plan, corresponding to slider position 33 here, between the first plan 10 and the "third navigation plan".

Both sliders cause one interpolation only, which is performed by the calculation core 150, during actuation of the setting buttons of the sliders along their plurality of intermediate positions. These intermediate plans generated on the basis of the movement of the two sliders 30, 40, are stored in the buffer 120 and can be retrieved when the slider is in the corresponding position.

When a user has found a plan beneficial to him, which he identifies as "good" based on the DVH diagram and which he considers useful also by virtue of the residual isodose partial images, he may export this beneficial plan to the data manager 160 by actuating button 47. This plan, which is the causal follow-up plan 20 in the example of FIG. 12, is the desired result.

This result is obtained from a number of—slider-induced—interpolations and the previously performed conversion of the first plan in two navigation plans 11, 12 using different mathematical weights but taking the one initial plan 10 as a basis.

Additional setting aids or indicators can be used which are designated by 45 and 46. Indicator 46 provides a measure of the size of the area changed as compared to the old plan.

One example is the arithmetic mean of the distance of all voxels to the initial voxel z1, the changes of which amount to more than 0.1 gy. In the example of FIG. 13, a deviation value of 41 is displayed by the indicator 46 as a measure of the area size. In the two images of FIGS. 10 and 11, this deviation value would be 60. The smaller this measure or indication of size, the slighter the deviation from the first plan 10 (initial plan), however, taking into account the specification of change in the small/local group of voxels z set in FIG. 7.

The generated follow-up plan of FIG. 13 is thus more favorable in terms of proximity to the first plan 10. When the user approves of this follow-up plan, it is transmitted as the causal follow-up plan 21 to the data manager 160 via button 47 and implemented therein in interface 161 for transfer to the device TG to be set.

The proximity of the DVH characteristics shown in pairs, e.g. the characteristics 80, 80' for the target volume of the first tumor, is particularly clear in FIG. 13.

This is shown further enlarged in FIG. 14.

Hardly any difference between the two characteristics 80, 80' can be seen in FIG. 14 and also the second tumor with the two characteristics 81, 81' hardly reveals any difference in the progress of the DVH family of characteristics. Slight differences can be seen in the curves (also: characteristics) of two other organs representing the spinal cord by DVH characteristics 82 and 82' and the right parotid gland by DVH characteristics 83, 83'.

The initial voxel z1 was located close to or in the right parotid gland. The change in its DVH characteristic 83 according to FIG. 5 as compared to the setting according to FIG. 13 can be seen more clearly and is denoted by 83'.

If one wishes to provide a measure of how the characteristics of the DVH distribution behave with respect to their proximity to the original plan 10, one could say in a first approximation that they, the curves (characteristics) of the DVH partial image 70, should not deviate by more than 5%. This is shown particularly well in partial image 70", is optically comprehensible and apparent from FIG. 14 as a cutout enlargement. Of course, this pertains only to the causal follow-up plan generated by the stages or steps explained within the scope of the embodiments. Other plans, including the first or second navigation plan, may deviate more clearly, since they are not required to represent the causal follow-up plan 20 or 21 but only open up an aid for virtually continuous navigation, wherein three plans are available as "basic plans", i.e. the first plan 10 and two navigation plans 11, 12 converted therefrom.

We claim:

1. A method for adjusting a dose distribution setting of a technical device for tumor therapy, comprising:
   reading a first plan from a data memory;
   displaying the first plan of a dose distribution in a plan volume on a display device for a possible setting of the technical device for tumor therapy for delivering the set dose distribution to a patient, wherein a first operating aid and a second operating aid are provided and each having two end positions, the first end position of the first operating aid corresponds to the first plan, wherein the second operating aid has a plurality of intermediate positions, each of which corresponds to an intermediate plan, each of the intermediate plans corresponding to an interpolation between a first navigation plan and a second navigation plan, and a selected intermediate position defining a selected third navigation plan as a mixed plan, and wherein the selected intermediate position of the second operating aid determines the second end position of the first operating aid;

changing or amending the first plan in at least one volume-specified fineness and drawing up or determining a causal follow-up plan by:

presetting of a new dose value for a local group of voxels in a volume-specified fineness at a certain position of the plan volume, which does not have this new dose value, wherein the certain position is determined by selecting an initial voxel located in a layer of the plan volume;

converting the first plan into the first navigation plan taking into account the first plan and a dose change in the local group of voxels; and converting the first plan into the second navigation plan in accordance with the first conversion and with presetting of mathematical weights in the conversion so that first and second navigation plans are different, the mathematical weights increase with increasing distance from the initial voxel, and the second navigation plan has more locally limited changes compared with the first navigation plan;

between the two end positions of the first operating aid there are a plurality of intermediate positions, each of which corresponds to an intermediate plan, and each of the intermediate plans corresponds to an interpolation between the first plan in the direction of the third navigation plan; and displaying a plan on the display device, corresponding to a setting of the first operating aid.

2. The method of claim 1, wherein the intermediate plans correspond to a dose distribution in the plan volume for a corresponding adjustment of the technical device.

3. The method of claim 1, wherein the interpolated intermediate plans are not stored in a database.

4. The method of claim 1, wherein the local group of voxels comprises less than 500 voxels and the plan volume comprises more than 2000 voxels.

5. The method of claim 1, wherein the local group is less than 5% of the plan volume.

6. The method of claim 1, wherein the mathematical weights are determined in a direction starting from the initial voxel depending on the respective tissue.

7. The method of claim 1, wherein a center setting of the first operating aid displays an intermediate plan on the display device that is an interpolation between the first plan and the third navigation plan.

8. The method of claim 1, wherein the first operating aid and the second operating aid are both displayed on the display device.

9. The method of claim 1, wherein the second operating aid has two end positions, one end position corresponding to the first navigation plan and the other end position corresponding to the second navigation plan.

10. The method of claim 1, wherein the first operating aid is one of a slider and a rotational element.

11. The method of claim 1, wherein the second operating aid is one of a slider and a rotational element.

12. The method of claim 1, wherein:

the first operating aid is arranged perpendicularly from the second operating aid and the first and second operating aids form a triangle, and the first operating aid and second operating aid comprise planar actuators.

13. A method for adjusting a dose distribution setting of a technical device for tumor therapy, comprising:

reading a first plan from a data memory;

displaying the first plan of a dose distribution in a plan volume on a display device for a possible setting of the technical device for tumor therapy for delivering the set dose distribution to a patient, wherein a first operating aid and a second operating aid are provided and each having two end positions, the first end position of the first operating aid corresponds to the first plan, wherein the second operating aid has a plurality of intermediate positions, each of which corresponds to an intermediate plan, each of the intermediate plans corresponding to an interpolation between a first navigation plan and a second navigation plan, and a selected intermediate position defining a selected third navigation plan; and wherein the selected intermediate position of the second operating aid determines the second end position of the first operating aid;

changing the first plan in no more than a volume-specified fineness comprising no more than a local group of voxels at a time and determining a causal follow-up plan by:

defining a new dose value for the local group of voxels in the volume-specified fineness at a certain position of the plan volume, which does not have this new dose value, wherein the certain position is determined by selecting an initial voxel located in a layer of the plan volume;

converting the first plan into the first navigation plan taking into account the first plan and a dose change in the local group of voxels;

and converting the first plan into the second navigation plan in accordance with the first conversion and with presetting of mathematical weights in the conversion so that first and second navigation plans are different;

wherein between the two end positions of the first operating aid there are a plurality of intermediate positions, each of which corresponds to an intermediate plan, and each of the intermediate plans corresponds to an interpolation between the first plan in the direction of the third navigation plan; and displaying a plan on the display device, corresponding to settings of the first and second operating aids.

14. The method of claim 13, wherein the intermediate plans correspond to a dose distribution in the plan volume for a corresponding adjustment of the technical device.

15. The method of claim 13, wherein the interpolated intermediate plans are not stored in a database.

16. The method of claim 13, wherein the local group is less than 5% of the plan volume.

17. The method of claim 16, wherein the local group of voxels comprises less than 500 voxels and the plan volume comprises more than 2000 voxels.

18. The method of claim 13, wherein mathematical weights are determined in a direction starting from the initial voxel depending on the respective tissue.

19. The method of claim 13, wherein a center setting of the first operating aid displays an intermediate plan on the display device that is an interpolation between the first plan and the third navigation plan.

20. The method of claim 13, wherein the second operating aid has two end positions, one end position corresponding to the first navigation plan and the other end position corresponding to the second navigation plan.

21. The method of claim 13, wherein the first operating aid and the second operating aid are both displayed on the display device.

22. The method of claim 13, wherein the first operating aid and/or the second operating aid comprise a slider and a rotational element.

* * * * *